(12) United States Patent
Kato et al.

(10) Patent No.: US 10,640,480 B2
(45) Date of Patent: May 5, 2020

(54) GNETIN C-RICH MELINJO EXTRACT AND PRODUCTION METHOD THEREOF

(71) Applicants: Hosoda SHC Co., Ltd., Fukui-shi, Fukui (JP); PERKUMPULAN MELINJO INDONESIA, Yogyakarta (ID)

(72) Inventors: Eishin Kato, Fukui (JP); Shinya Hosoda, Fukui (JP)

(73) Assignees: HOSODA SHC CO., LTD., Fukui (JP); PERKUMPULAN MELINJO INDONESIA, Yogyakarta (ID)

(*) Notice: Subject to any disclaimer, the term of this patent is extended or adjusted under 35 U.S.C. 154(b) by 84 days.

(21) Appl. No.: 15/579,770

(22) PCT Filed: Jul. 28, 2017

(86) PCT No.: PCT/JP2017/027556
§ 371 (c)(1),
(2) Date: Dec. 5, 2017

(87) PCT Pub. No.: WO2019/021485
PCT Pub. Date: Jan. 31, 2019

(65) Prior Publication Data
US 2019/0031635 A1  Jan. 31, 2019

(51) Int. Cl.
*A61K 36/00* (2006.01)
*C07D 307/80* (2006.01)

(52) U.S. Cl.
CPC .................. *C07D 307/80* (2013.01)

(58) Field of Classification Search
None
See application file for complete search history.

(56) References Cited

U.S. PATENT DOCUMENTS

| | | | |
|---|---|---|---|
| 5,763,389 | A | 6/1998 | Shen et al. |
| 8,067,036 | B2 | 11/2011 | Kato et al. |
| 2008/0274218 | A1 | 11/2008 | Kato et al. |
| 2014/0072692 | A1* | 3/2014 | Yamada ............. A23L 19/09 |
| | | | 426/614 |

FOREIGN PATENT DOCUMENTS

| | | |
|---|---|---|
| CN | 102977179 A | 3/2013 |
| JP | 09-503781 | 4/1997 |
| JP | 2009-13123 A | 1/2009 |
| JP | 2009-046446 A | 3/2009 |
| JP | 2009-247254 A | 10/2009 |
| JP | 2009-249320 A | 10/2009 |
| JP | 2011-079797 A | 4/2011 |
| JP | 4744447 B | 8/2011 |
| JP | 4975069 B | 7/2012 |
| JP | 2013-082701 A | 5/2013 |
| JP | 2015-218146 A | 12/2015 |
| WO | 2006/030771 A1 | 3/2006 |

OTHER PUBLICATIONS

Bhat et al, Evaluating belinjau (*Gnetum gnemon* L.) seed flour quality as a base for development of novel food products and food formulations. Food chemistry, (Aug. 1, 2004) vol. 156, pp. 42-49 (Year: 2014).*
International Search Report and Written Opinion, International Patent Application No. PCT/JP2017/027556, dated May 9, 2017 (11 pages).

* cited by examiner

*Primary Examiner* — Qiuwen Mi
(74) *Attorney, Agent, or Firm* — Hamre, Schumann, Mueller & Larson, P.C.

(57) ABSTRACT

To provide a gnetin C high content melinjo extract rich in the content of gnetin C which is useful for prevention and/or treatment of diseases such as metabolic syndrome, diabetes mellitus, hypertension, gout, cancer, collagen disease, periodontal disease and the like and further for beauty care and/or protection of skin and of which intake/dosage or use amount can be reduced. An extract is extracted from melinjo fruit, by using an extraction solvent which is a mixed solvent obtained by blending at least one of an emulsifier, a cycrodextrin and an acid into water and/or an organic solvent.

10 Claims, 7 Drawing Sheets

Comparative Example 3

Fig.4

Example 1

Fig.5

Example 2

Fig.6

Example 4

Fig.7

Example 5

Fig.8

Example 7

GNETIN C-RICH MELINJO EXTRACT AND PRODUCTION METHOD THEREOF

TECHNICAL FIELD

The present invention relates to a melinjo extract rich in gnetin C represented by the following formula (1) and a production method thereof.

[Chemical Formula 1]

(1)

BACKGROUND ART

It is disclosed that the melinjo components have various biological actions. Patent document 1, Patent document 2 and Non-Patent document 1 disclose an antioxidant action, an antibacterial action, a lipase inhibitory action and an amylase inhibitory action of gnetin C, Non-Patent document 2 discloses an angiogenesis suppressive action and an antitumor action of gnetin C, Non-Patent document 3 discloses an antitumor action of gnetin C, Non-Patent document 4 discloses an apoptosis induction action of gnetin C in human leukemia cells, Patent document 3 and Non-Patent document 5 disclose an immunostimulating action of a melinjo extract, Non-Patent document 6 discloses an antibacterial action of a melinjo extract, Patent document 4, Non-Patent document 7 and Non-Patent document 8 disclose an anti-obesity/diabetes improving action of a melinjo extract, Patent document 5 and Non-Patent document 9 disclose a tyrosinase inhibitory action and a melanin biosynthesis inhibitory action of gnetin C, Non-Patent document 10 discloses a vascular aging suppressive action of a melinjo extract, Patent document 6 discloses anti-aging by a sirtuin activating action of gnetin C, Patent document 7 discloses an angiotensin converting enzyme inhibitory action of a melinjo extract, Non-Patent document 11 discloses a serum uric acid level lowering action of a melinjo extract, Non-Patent document 12 discloses a periodontal disease exacerbation preventing action of a melinjo extract, Non-Patent document 13 discloses an atrophic skin suppressive action, Non-Patent document 14 discloses an immunomodulating action of a melinjo extract, and Non-Patent document 15 discloses an AMPK phosphorylation elevating action of a melinjo extract in liver of a newborn female child of a fructose excessively ingested pregnant rat. Further, safety of a melinjo extract is also recognized since the melinjo extract shows a high density lipoprotein (HDL) cholesterol increasing action and a uric acid level lowering action without showing any abnormalities in a toxicity test in rats (Non-Patent document 16) and a safety test in humans (Non-Patent document 17), and exerts no influence on the anti-coagulant activity of a hepatic metabolizing enzyme cytochrome P-450 and warfarin (Non-Patent document 18). Further, it is reported that gnetin C exerts a more antiproliferative effect than that of medicinal products on leukemia cells of a patient (Non-Patent document 19).

The main component contained in endosperm of a melinjo seed is gnemonoside A as a glycoside of gnetin C represented by the following formula (2), and it is already disclosed that the component showing the actions described above is gnetin C as an aglycon represented by the above-described formula (1). Patent document 1 discloses a production method of a Gnetaceae extract comprising aging at ordinary temperature to 70° C. utilizing generation of gnetin C by an enzymatic reaction during the aging, and since the content of gnetin C in the Gnetaceae extract is less than 15%, the amount of intake thereof tends to increase for obtaining the various effects described above. Promotion of an enzymatic reaction in aging is not disclosed and also is not suggested in any of the above-described documents. Further, the method for investigating generated state is only a qualitative test by ultraviolet absorption spectrum and thin layer chromatogram (TLC).

[Chemical Formula 2]

(2)

(It is gnemonoside A when $R_1$ and $R_2$ represent a glucopyranosyl group, gnemonoside C when $R_1$ represents a glucopyranosyl group and $R_2$ represents hydrogen, and gnemonoside D when $R_1$ represents hydrogen and $R_2$ represents a glucopyranosyl group, in the formula.)

RELATED ART DOCUMENT

Patent Document

[Patent document 1] Japanese Patent No. 4744447 (U.S. Pat. No. 8,067,036, EU Patent No. 1790239, Chinese Patent No. 892494)
[Patent document 2] JP-A No. 2009-13123
[Patent document 3] JP-A No. 2009-46446
[Patent document 4] JP-A No. 2009-249320
[Patent document 5] Japanese Patent No. 4975069
[Patent document 6] JP-A No. 2011-79797
[Patent document 7] JP-A No. 2013-82701

Non-Patent Document

[Non-Patent document 1] JOURNAL OF AGRICULTURAL AND FOOD CHEMISTRY, 2009, 57, 2544-2549
[Non-Patent document 2] MOLECULAR NUTRITION FOOD RESEARCH, 2011, 55, 1730-1734

[Non-Patent document 3] CANCER MEDICINE 2015, 4, 1767-1780
[Non-Patent document 4] BIOLOGICAL AND PHARMACEUTICAL BULLETIN, 2006, 29, 1490-1492
[Non-Patent document 5] PLANTA MEDICA, 2011, 77, 1027-1034
[Non-Patent document 6] MICROBIOLOGY INDONESIA, 2011, 5, 103-112
[Non-Patent document 7] FOOD STYLE, 2012, 16, 20-22
[Non-Patent document 8] BIOSCIENCE, BIOTECHNOLOGY, AND BIOCHEMISTRY, 2015, 79, 2044-2049
[Non-Patent document 9] BIOLOGICAL AND PHARMACEUTICAL BULLETIN, 2012, 35, 993-996
[Non-Patent document 10] JOURNAL OF NATURAL PRODUCTS, 2013, 76, 1242-1247
[Non-Patent document 11] EVIDENCE-BASED COMPLEMENTARY AND ALTERNATIVE MEDICINE VOLUME 2013, ARTICLE ID 589169, 9PAGES
[Non-Patent document 12] FREE RADICAL BIOLOGY AND MEDICINE, 2014, 75, 222-229
[Non-Patent document 13] OXIDATIVE MEDICINE AND CELLULAR LONGEVITY, VOLUME 2015, ARTICLE ID 391075, 8PAGES
[Non-Patent document 14] INTEGRATIVE MOLECULAR MEDICINE, 2015, 2, 405-413
[Non-Patent document 15] REPRODUCTIVE BIOLOGY, 2016, 16, 165-173
[Non-Patent document 16] FOOD AND CHEMICAL TOXICOLOGY, 2014, 6, 230-235
[Non-Patent document 17] JOURNAL OF AGRICULTURAL AND FOOD CHEMISTRY, 2014, 62, 1999-2007
[Non-Patent document 18] JOURNAL OF ATHEROSCLEROSIS AND THROMBOSIS, 2016, 23, 1099-1110
[Non-Patent document 19] CANCER LETTERS, 2017, 400, 127-136

SUMMARY OF THE INVENTION

Problems to be Solved by the Invention

In view of the above descriptions, the present invention has an object of providing a gnetin C-high content melinjo extract rich in the content of gnetin C useful for prevention and/or treatment of diseases such as metabolic syndrome, diabetes mellitus, hypertension, gout, cancer, collagen disease, periodontal disease, leukemia and the like, further for beauty care and/or protection of skin, of which the intake/dosage or use amount thereof can be reduced because of the increased content of gnetin C showing various biological actions.

Means for Solving the Problem

The present inventors have intensively studied for solving the above-described problem and resultantly found that by allowing an emulsifier, a cycrodextrin, an acid and the like to coexist in water and/or an organic solvent and using the resultant solution as an extraction solvent, a solvolysis reaction of a glycoside of gnetin C is promoted and a melinjo extract having the enhanced content of gnetin C can be produced, leading to completion of the present invention.

The present invention for solving the above-described problem is a production method of a melinjo extract, comprising an extraction step of extracting an extract from melinjo fruit by using an extraction solvent which is a mixed solvent obtained by blending at least one of an emulsifier, a cycrodextrin and an acid into water and/or an organic solvent.

By using a mixed solvent obtained by blending at least one of an emulsifier, a cycrodextrin and an acid into water and/or an organic solvent as an extraction solvent, the solvolysis reaction is promoted in a process of action of glucosidase contained in endosperm to cause elimination of one glucose from gnemonoside A (in the chemical formula 2, $R_1$ and $R_2$ represent a glucopyranosyl group) as the main component to generate gnemonoside C (in the formula 2, $R_1$ represents a glucopyranosyl group and $R_2$ represents hydrogen) and gnemonoside D (in the chemical formula 2, $R_1$ represents hydrogen and $R_2$ represents a glucopyranosyl group) then elimination of another glucose to cause changing to gnetin C, thus, a melinjo extract having remarkably high gnetin C content can be produced.

In a preferable embodiment of the present invention, the above-described melinjo fruit is melinjo endosperm.

By using melinjo endosperm, a melinjo extract having the higher content of gnetin C can be produced.

In a preferable embodiment of the present invention, the above-described organic solvent is one or more selected from ethanol, ethyl acetate and acetone.

By using the compounds described above as the organic solvent, a melinjo extract having the higher content of gnetin C can be produced.

In a preferable embodiment of the present invention, the above-described emulsifier is one or more selected from glycerin fatty acid ester, sucrose fatty acid ester, sorbitan fatty acid ester, soybean lecithin and sodium stearate.

By using the compounds described above as the emulsifier, a melinjo extract having the higher content of gnetin C can be produced.

In a preferable embodiment of the present invention, the above-described acid is one or more selected from acetic acid, lactic acid, citric acid, adipic acid, hydrochloric acid and phosphoric acid.

By using the compounds described above as the acid, a melinjo extract having the higher content of gnetin C can be produced.

In a preferable embodiment of the present invention, the temperature of the extraction solvent in extracting is 10 to 70° C.

By conducting extraction in the above-described temperature range, a melinjo extract having the higher content of gnetin C can be produced.

The present invention for solving the above-described problem is a melinjo extract produced by the production method of a melinjo extract described above.

The melinjo extract of the present invention has the remarkably high content of gnetin C, and is useful for prevention and/or treatment of diseases such as metabolic syndrome, diabetes mellitus, hypertension, gout, cancer, collagen disease, periodontal disease and the like and further for beauty care and/or protection of skin, even if the intake/dosage or use amount thereof is small.

The present invention for solving the above-described problem is a production method of a melinjo extract-containing composition, comprising a step of adding the above-described melinjo extract.

In a preferable embodiment of the present invention, a step of adding a carbohydrate is further included, and the above-described melinjo extract-containing composition is powdery.

In a preferable embodiment of the present invention, a step of adding a fat and oil is further included, and the above-described melinjo extract-containing composition is oily to waxy.

In a preferable embodiment of the present invention, the above-described melinjo extract-containing composition is a food and drink, a medicinal product or a cosmetic.

Effect of the Invention

According to the present invention, a gnetin C high content melinjo extract can be produced by converting gnemonoside A, gnemonoside C and gnemonoside D as glycosides into gnetin C as an aglycon by elevating the solvolysis reaction rate by helping the work of glucosidase catalyzing solvolysis of a glucoside bond, and the use amount of the melinjo extract decreases and the application of the preparation expands, thus, the present invention can contribute widely to prevention and/or treatment of aging, cancer, leukemia, malignant melanoma, periodontal disease, pollen disease, metabolic syndrome, diabetes mellitus, cardiac disease, brain disease, allergic disease, autoimmune disease, atopic dermatitis, hyperuricemia, gout and the like by various actions such as an antioxidant action, an antibacterial action, a lipase inhibitory action, an amylase inhibitory action, an angiogenesis suppressive action, an antitumor action, an action of inducing apoptosis of human leukemia cells, an immunostimulating action, an immunomodulating action, an anti-obesity/diabetes improving action, a tyrosinase inhibitory action, a melanin biosynthesis inhibitory action, a vascular aging suppressive action, a sirtuin activating action, a high density lipoprotein (HDL) cholesterol increasing action, a uric acid level lowering action, a periodontal disease exacerbation preventing action, an atrophic skin suppressive action and the like.

As described above, a gnetin C-high content melinjo extract having the enhanced content of gnetin C obtained by using safe Gnetaceae melinjo often eaten in Southeast Asia as a raw material can contribute to prevention or treatment of various diseases in daily life.

BEST MODES FOR CARRYING OUT THE INVENTION

Embodiments of the present invention will be illustrated below.

Gnetin C in the present invention is represented by the following formula (1).

[Chemical Formula 3]

(1)

Gnemonosides A, C and D are represented by the following formula (2).

[Chemical Formula 4]

(2)

(It is gnemonoside A when $R_1$ and $R_2$ represent a glucopyranosyl group, gnemonoside C when $R_1$ represents a glucopyranosyl group and $R_2$ represents hydrogen, and gnemonoside D when R₁ represents hydrogen and R₂ represents a glucopyranosyl group, in the formula.)

Gnetin L is represented by the following formula (3).

[Chemical Formula 5]

(3)

Melinjo referred to in the present invention is the Japanese reading of Indonesian name Melinjo, and its botanical name is *Gnetum gnemon* L. (English name *Gnemon* tree), and in Japan, it is called *Gnetum* and the tree of *Gnemon*, and is a plant of Gnetaceae family. Melinjo is cultivated widely in Southeast Asia, and immature fruits, young leaves and flowers thereof are used as vegetables in soups and stews, and seeds of mature fruits are heated before peeling of seed skin and crush thereof, then, dried to obtain emping which is fried in an oil and eaten.

In the production method of a melinjo extract of the present invention, melinjo fruit can be used. The above-described melinjo fruit is composed of fruit skin (epicarp) and seed, and the above-described seed is composed of seed coat (endocarp), thin skin (seed coat) and endosperm (germ, albumen). Though any of these portions can be used, endosperm containing glucosidase is preferably used. Further, stems and roots may coexist and be used in the above-described melinjo fruit and melinjo seed.

As the above-described melinjo fruit, any of immature fruits and fully matured fruits can be used, and matured fruits are preferable. Further, as the above-described melinjo fruit, any of raw (undried) fruits and fruits dried in the sun or by a drying machine (70° C. or higher) may be used.

Emping and those heated in its production (70° C. or higher) also can be used together with at least one of non-heated melinjo fruit, seed and endosperm.

Melinjo fruit can be used in any of sliced and fractured/powdered forms.

In the production method of a melinjo extract of the present invention, at least one of an emulsifier, a cycrodextrin or an acid is mixed into water and/or an organic solvent and the mixed solvent thereof is used as an extraction solvent.

By mixing an emulsifier, a cycrodextrin or an acid, the solvolysis reaction by glucosidase can be promoted, and a melinjo extract rich in gnetin C can be produced.

In the present specification, the melinjo extract denotes an extraction liquid of melinjo or its concentrate.

As the organic solvent, any of hydrophilic solvents and hydrophobic solvents may be used, and the hydrophilic solvent includes alcohols: methanol, ethanol, 1-propanol, 2-propanol, 1-butanol, ethylene glycol, propylene glycol, butylene glycol, glycerol and the like, ethers: diethyl ether, cellosolve, dioxane, tetrahydrofuran and the like, esters: methyl acetate, ethyl acetate, cellosolve acetate and the like, ketones: acetone, methyl ethyl ketone and the like, amines: 2-aminoethanol, pyridine, monomethanolamine and the like, amides: dimethylformamide, N,N-dimethylacetamide and the like, sulfoxides: dimethyl sulfoxide, nitriles: acetonitrile, etc.

The hydrophobic solvent includes hydrocarbons: hexane, cyclohexane, heptane, benzene, toluene, xylene and the like, halogenated hydrocarbons: methylene chloride, chloroform, 1, 2-dichloroethane, dichloroethylene, trichloroethylene and the like, etc.

The organic solvents mentioned above may be used each singly or two or more of them may be mixed and used.

As the organic solvent, one or more selected from ethanol, ethyl acetate and acetone are preferably used.

By using the above-described specific organic solvent, the solvolysis reaction can be promoted more.

The emulsifier used in the production method of the present invention is a so-called surfactant, and any of synthetic surfactants and natural surfactants may be used.

The synthetic surfactants include glycerin fatty acid esters: glycerol monocaprylate, glycerol monooleate, glycerol monostearate, glycerol dioleate, glycerol distearate and the like, polyglycerol fatty acid esters: diglycerol oleic acid ester, diglycerol stearic acid ester, tetraglycerol stearic acid ester, decaglycerol caprylic acid ester, decaglycerol lauric acid ester, decaglycerol myristic acid ester, decaglycerol stearic acid ester, decaglycerol oleic acid ester, decaglycerol behenic acid ester and the like, sucrose fatty acid esters: sucrose lauric acid ester, sucrose myristic acid ester, sucrose oleic acid ester, sucrose stearic acid ester, sucrose erucic acid ester, sucrose oleic acid palmitic acid stearic acid ester and the like, sorbitan fatty acid esters: sorbitan caprylate, sorbitan laurate, sorbitan stearate, sorbitan oleate, sorbitan trioleate, polyoxyethylenesorbitan monolaurate, polyoxyethylenesorbitan monostearate, polyoxyethylenesorbitan monooleate, polyoxyethylenesorbitan monopalmitate, polyoxyethylenesorbitan tristearate, polyoxyethylenesorbitan trioleate and the like, propylene glycol fatty acid esters: propylene glycol monolaurate, propylene glycol monopalmitate, propylene glycol monostearate, propylene glycol monooleate, propylene glycol monobehenate and the like, fatty acid sodium: sodium laurate, sodium oleate, sodium palmitate, sodium stearate and the like, others: oxyethylene fatty acid alcohols, morpholine fatty acid salts and the like, etc.

The natural surfactants include lecithins such as soybean lecithin, egg-yolk lecithin and lysolecithin, and phospholipids such as krill oil and the like, casein sodium, *quillaja* saponin and the like.

Further, a mixture obtained by mixing two or more selected from the above-described emulsifiers can be used.

As the emulsifier in the present invention, an emulsifier forming micelle in the extraction liquid is preferable.

As the emulsifier in the present invention, one or more selected form glycerol fatty acid ester, sucrose fatty acid ester, sorbitan fatty acid ester, soybean lecithin and sodium stearate are more preferably used.

By using these emulsifiers, a melinjo extract having the higher content of gnetin C can be produced.

The blending amount of the emulsifier is preferably 0.002 to 0.2 parts, more preferably 0.005 to 0.1 parts with respect to 1 part of the dry weight of an extraction feed.

Within the above-described range, the solvolysis reaction can be promoted more, and a melinjo extract having the high content of gnetin C can be produced.

The cycrodextrin used in the present invention is also a cyclic oligosaccharide, and includes inclusion agents such as α-, β- and γ-cyclodextrins, branched cyclodextrin, cycloamylose and the like and highly branched cycrodextrin and the like, and if necessary, these can be mixed and used. The blending amount of the cycrodextrin is preferably 0.003 to 0.5 parts, more preferably 0.005 to 0.3 parts with respect to 1 part of the dry weight of an extraction feed.

Within the above-described range, the solvolysis reaction can be promoted more, and a melinjo extract having the high content of gnetin C can be produced.

The acid used in the production method of the present invention may be any of an organic acid and an inorganic acid, and the organic acid includes formic acid, acetic acid, propionic acid, butyric acid, lactic acid, succinic acid, fumaric acid, tartaric acid, citric acid, adipic acid, trifluoroacetic acid, methanesulfonic acid, p-toluenesulfonic acid, and further, rice vinegar, cereal vinegar, apple-cider vinegar and the like instead of acetic acid, and the inorganic acid includes hydrochloric acid, sulfuric acid, phosphoric acid, boron trifluoride diethyl ether complex and the like, etc. and if necessary, a mixed acid obtained by mixing two or more of the above-described acids can be used, and it is preferable to carry out extraction in a mildly acidic range of pH 3 to 6.5.

By carrying out extraction in the above-described pH range, the solvolysis reaction by glucosidase can be promoted more, and a melinjo extract having the high content of gnetin C can be produced.

The melinjo extract of the present invention can be produced as described below.

An extract is extracted from melinjo fruit by using as an extraction solvent the mixed solvent obtained by blending at least one of an emulsifier, a cycrodextrin and an acid described above. It is preferable that the above-described melinjo fruit is immersed in the above-described extraction solvent. When melinjo fruit is immersed in an extraction solvent, gnetin C is generated by promoting the solvolysis reaction by glucosidase in endosperm, if necessary while stirring and if necessary with heating (up to around 70° C.). Heating is conducted by using a heating device equipped with a sensor capable of regulating to desired temperature, and heat sources such as electricity, gas, steam and the like can be utilized.

The extraction temperature is preferably 10 to 70° C., more preferably 30 to 60° C.

When the extraction temperature is 30 to 60° C., the action of glucosidase can be activated more.

As the glucosidase, glucosidase having the same action as that of glucosidase contained in melinjo, and microorganisms and animal and plant tissues containing it may be added, and it is preferable to use glucosidase originally contained in melinjo fruit.

By using glucosidase originally contained in melinjo fruit, labor hour and cost for production of a melinjo extract can be reduced.

The immersion liquid having progressed the solvolysis reaction is filtrated to remove insoluble materials, the filtrate is concentrated under ordinary pressure or reduced pressure and the solvent is distilled off to give a syrupy or resinous concentrate, thus, the melinjo extract of the present invention can be obtained. Also, the resinous melinjo extract of the present invention rich in gnetin C can be obtained by extracting the filtrate with an organic solvent such as ethyl acetate and the like, then, concentrating the organic layer under ordinary pressure or reduced pressure. Alternatively, the melinjo extract of the present invention can be obtained also by freeze-drying or spray-drying the filtrate. Further, high purity gnetin C can be obtained by purifying the concentrate by a polystyrene adsorption resin, silica gel column chromatography, reversed phase column chromatography or gel filtration chromatography and the like, if necessary.

The generation state of gnetin C can be checked by using high performance liquid chromatographic method (hereinafter, abbreviated as HPLC).

Analysis conditions of HPLC are as shown below, and the retention times of gnemonoside A, gnemonoside D, gnemonoside C, gnetin C and gnetin L are around 8.5 minutes, 22.5 minutes, 24 minutes, 32.5 minutes and 33.8 minutes, respectively.

Column: octadecylsilyl (ODS)

Mobile phase: 1% acetic acid aqueous solution (liquid A), 1% acetic acid-containing acetonitrile (liquid B)

Liquid B is flowed for 10 minutes at a linear gradient from 20% to 22%, for 10 minutes at a linear gradient from 22% to 30%, and for 15 minutes at 37%

Flow rate: 0.8 mL/min

Analysis time: 45 minutes

Detection wavelength: 320 nm

For the melinjo extract of the present invention, the proportion of GCA to TGA which is the sum of GCA and GGA on the chromatogram obtained by HPLC measurement is preferably 35% or more, more preferably 40% or more, more preferably 45% or more, further preferably 50% or more.

Further, for the melinjo extract of the present invention, GLA/GCA is preferably 0.13 or less, more preferably 0.12 or less, further preferably 0.11 or less.

In the present specification, the terms GCA, GGA, TGA and GLA are defined as below.

GCA=peak area of gnetin C

GGA=peak area of gnemonoside A+peak area of gnemonoside C+peak area of gnemonoside D

TGA=GCA+GGA

GLA=peak area of gnetin L

Proportion (%) of GCA to TGA=100GCA/TGA

Area ratio of GLA to GCA=GLA/GCA

Additives can be added to the above-described melinjo extract according to the intended dosage form.

For example, a carbohydrate can be added to a melinjo extract, to give a powdery melinjo extract-containing composition.

The carbohydrate which can be added includes monosaccharides such as glucose, sorbitol and the like, disaccharides such as lactose, lactitol, trehalose and the like, oligosaccharides such as dextrin, polydextrose and the like, cyclic sugars such as α-, β- and γ-cyclodextrins, branched cyclodextrin, cycloamylose and the like, starches, microcrystalline cellulose, substituted celluloses such as methyl cellulose, ethyl cellulose, hydroxy cellulose, carboxymethyl cellulose and the like, etc.

Also, a fat and oil can be added to a melinjo extract, to give an oily to waxy melinjo extract-containing composition.

The fat and oil which can be added includes vegetable oils such as olive oil, coconut oil, soybean oil, linseed oil, perilla oil and the like, fish oils, animal oils, waxes, and higher alcohols such as cetanol, oleyl alcohol and the like, etc.

In the melinjo extract and the melinjo extract-containing composition obtained as described above, 100GCA/TGA which is the proportion of gnetin C is remarkably high and GLA/GCA is low as compared with a conventional method of performing extraction together with aging utilizing an intra-endosperm enzyme.

The melinjo extract or the melinjo extract-containing composition having the high content of gnetin C as described above can be widely applied as a food and drink, a health food, a preventive agent and a treatment agent for prevention and/or treatment of various diseases as described above since the use amount thereof can be reduced.

When the solvolysis reaction of a glycoside is promoted, there is also a possibility that generation of gnetin L not of gnetin C is predominantly promoted. In contrast, the production method of the present invention can produce a melinjo extract rich in gnetin C as a useful component, not predominantly promoting generation of gnetin L. In other words, a melinjo extract having low GLA/GCA can be produced according to the production method of the present invention.

The melinjo extract-containing composition obtained by the production method of the present invention can be a food and drink.

The above-described food and drink can be a health food, further a food for specified health use, and if necessary, is produced by blending with various components conventionally used in foods.

As the food and drink form, all food and drink forms such as powdery (including granular) foods, solid foods, creamy or jam-like semiliquid foods, gelled foods and beverages, and the like are possible. Particularly, powdery foods are desirable because of excellent handling and portability. For example, preparations such as a powder, a granule, a tablet, a capsule, a drinkable preparation and the like; powder soft drinks containing a blended arbitrary base material usually used, liquid products such as liquid soft drink, juice, coffee, black tea, liqueur, milk, whey beverage, lactic acid bacteria beverages, yoghurt and the like; solid products such as candy, caramel, chewing gum, chocolate, gummi, ice cream, pudding, egg products, yokan (soft adzuki-bean jelly), mizu-yokan (soft adzuki-bean jelly), okaki (small rice cracker), rice cake, rice dumpling, rice cracker, crape, okonomiyaki (pancake), bread, cookie, noodles, hamburger, water paste, tempura, fermented foods, furikake (rice seasoning) and the like, are mentioned.

In foods and drinks of these forms, extracted materials of crude drugs/healthy teas/herbs such as ashitaba, ginkgo leaf, chamomile, mulberry, wolfberry, ginger, swertia, gymnema and the like can be added.

Further, sugar alcohols such as erythritol, sorbitol, maltitol, xylitol and the like, glucose, fructose, sucrose, lactose and dextrin, and the like may be mixed to prepare the food and drink.

When the melinjo extract-containing composition obtained by the production method of the present invention is used as the food and drink for improvement or prevention of metabolic syndrome, diabetes mellitus, hypertension, hyperuricemia, cancer, leukemia, malignant melanoma, collagen disease, periodontal disease, pollen disease and the like, the blending amount of the melinjo extract of the present invention is in the range of 0.01 to 90%, preferably in the range of 0.05 to 80% in terms of dry weight, in view of flavor and color tone as the food and drink.

In the above-described food and drink, sweeteners (1), sour agents (2), antioxidants (3), quality improving agents (4), starch materials (thickening agent, stabilizer, gelling agent) (5), nutrient enhancement agents (6) and seasoning agents (7) exemplified below can be added, according to the kind of the product. In addition, those which are used as general raw materials of food and drink_such as calcium salts, emulsifiers, coloring agents, inflating agents, flavoring agents, preserving agents and the like can be appropriately added to give a composition.

(1) glucose, fructose, sucrose, maltose, sorbitol, stevioside, glycyrrhizin, aspartame, rubusoside, corn syrup, lactose (2) citric acid, tartaric acid, malic acid, succinic acid, lactic acid (3) L-ascorbic acid, DL-α-tocopherol, sodium erythorbate (4) glycerin, propylene glycol (5) gum arabic, carrageenan, casein, gelatin, pectin, agar-agar, konjac flour, glucomannan, starch (6) vitamins, nicotinamide, calcium pantothenate, eicosapentaenoic acid (EPA), docosahexaenoic acid (DHA)

(7) amino acids, inosinic acids

The melinjo extract-containing composition obtained by the production method of the present invention can be a preventive agent and a treatment agent. The above-described preventive agent and the above-described treatment agent are preparations solidified by blending any auxiliary agents, excipients and the like if necessary or liquefied by appropriately blending water or an organic solvent and the like.

When the melinjo extract-containing composition obtained by the production method of the present invention is used as an oral agent for improvement and prevention or treatment of neurological diseases and the like, the dosage (administration dose) thereof varies depending on the target of administration and the states of the recipient (sex, age, body weight, degree of obesity, degree of general health and the like). Usually, the gnetin C high content melinjo extract can be administered in the range of 1 to 200 mg/kg body weight in terms of weight, as the daily dosage. Since the raw material melinjo is regularly eaten, administration in an amount over 200 mg/kg body weight causes no problem.

The melinjo extract-containing composition can be used not only as an oral agent but also as a skin preparation.

The melinjo extract-containing composition obtained by the production method of the present invention can be applied to whitening cosmetics for suppressing melanin formation and inflammation by sunburn, hair-growth medicines and epilation inhibitors, hygienic items for wound healing acceleration and the like, deodorant sanitary goods, and the like.

When used as the animal feeding stuff, the above-described various components can be appropriately blended to give a powder (including granule), a paste, a capsule, a syrup, a solid, a gel, a liquid (solution, suspension, emulsion) and the like. The animal feeding stuff includes feeding stuffs for domestic animals, and pet foods such as cat foods, dog foods, rabbit foods and the like.

EXAMPLE

Hereinafter, the present invention will be detailed by Examples, but is not limited to these Examples.

[Test 1] Preparation of Melinjo Extracts

Figure 1:
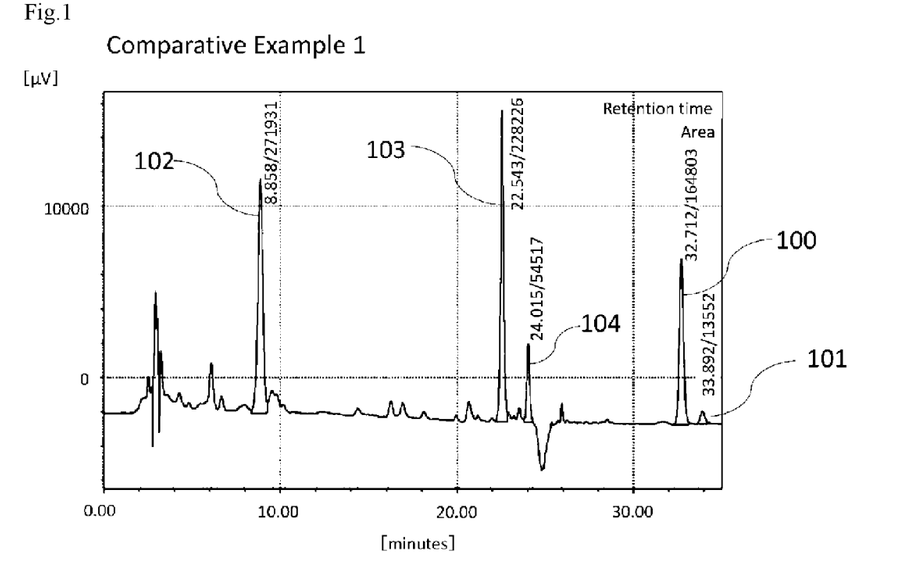
FIG. 1 is an HPLC chromatogram of a liquid obtained by dissolving the yellow-brown resinous melinjo extract obtained in Comparative Example 1 in 50% ethanol.
Figure 2:
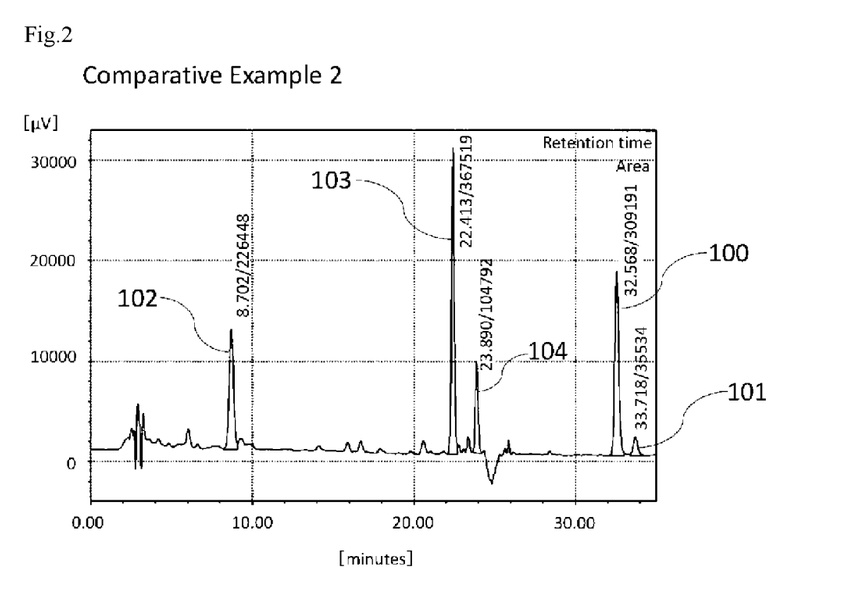
FIG. 2 is an HPLC chromatogram of a liquid obtained by dissolving the yellow-brown resinous melinjo extract obtained in Comparative Example 2 in 50% ethanol.
Figure 3:
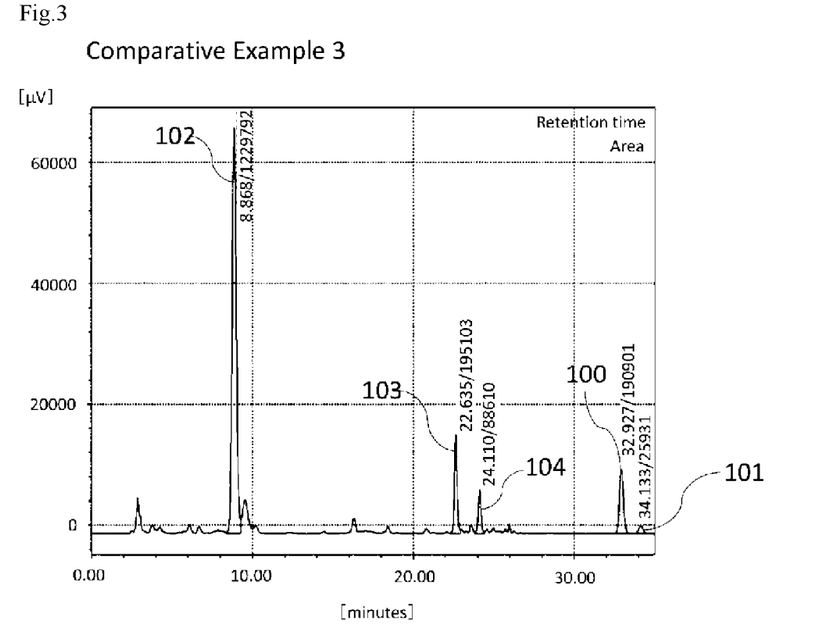
FIG. 3 is an HPLC chromatogram of a liquid obtained by dissolving the yellow-brown resinous melinjo extract obtained in Comparative Example 3 in 50% ethanol.
Figure 4:
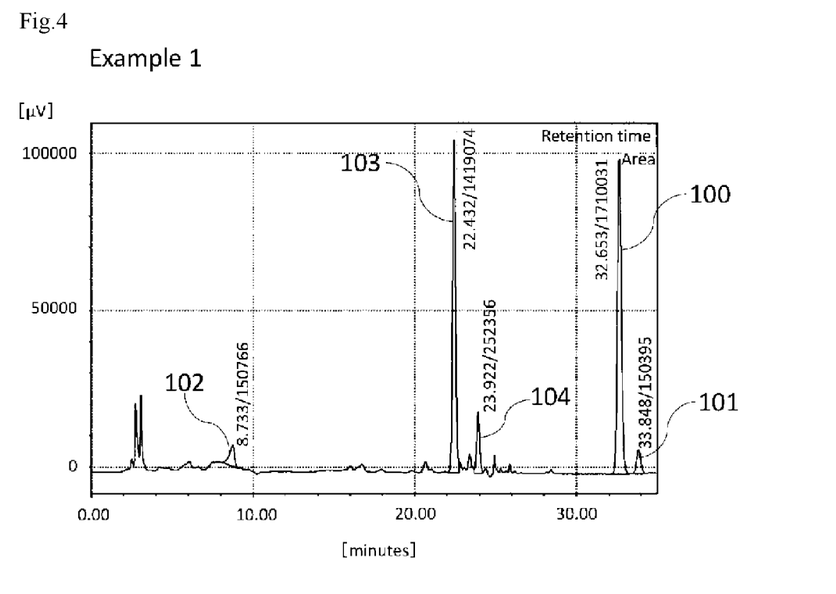
FIG. 4 is an HPLC chromatogram of a liquid obtained by dissolving the yellow-brown resinous melinjo extract obtained in Example 1 in 50% ethanol.
Figure 5:
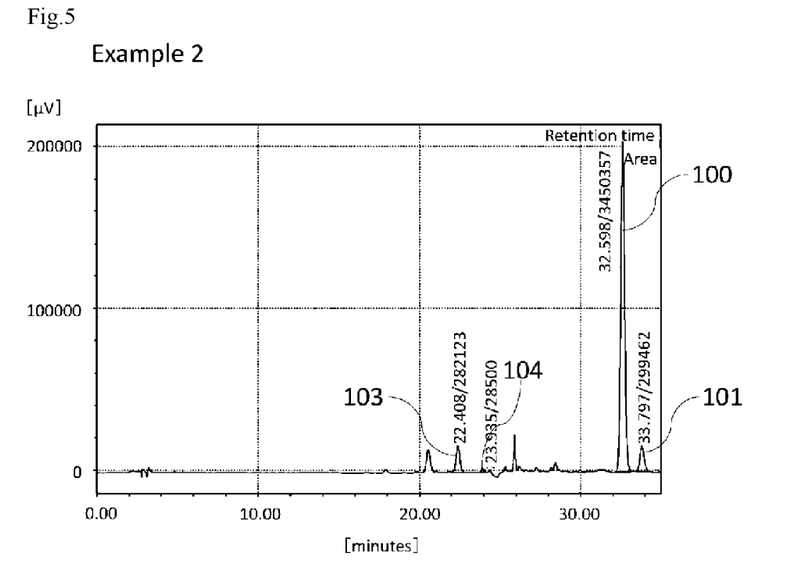
FIG. 5 is an HPLC chromatogram of a liquid obtained by dissolving the yellow-brown resinous melinjo extract obtained in Example 2 in 50% ethanol.
Figure 6:
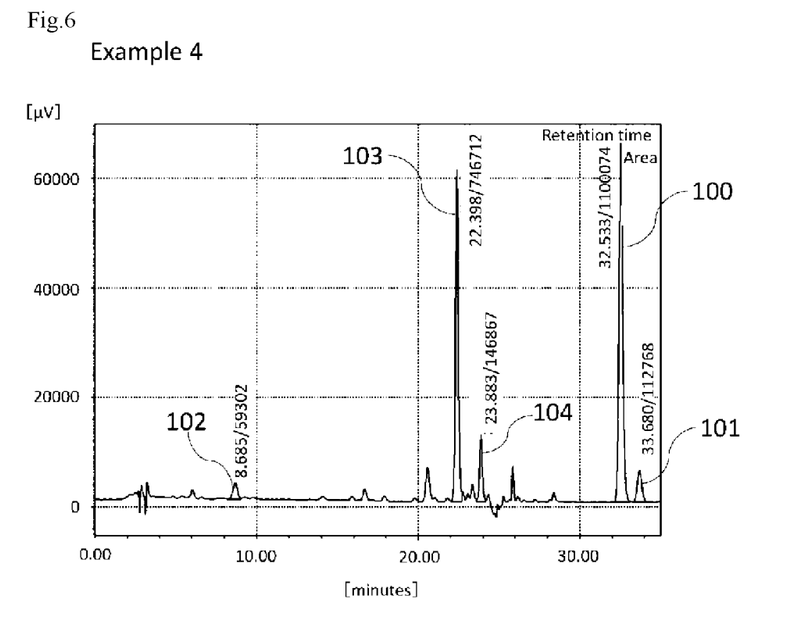
FIG. 6 is an HPLC chromatogram of a liquid obtained by dissolving the yellow-brown resinous melinjo extract obtained in Example 4 in 50% ethanol.
Figure 7:
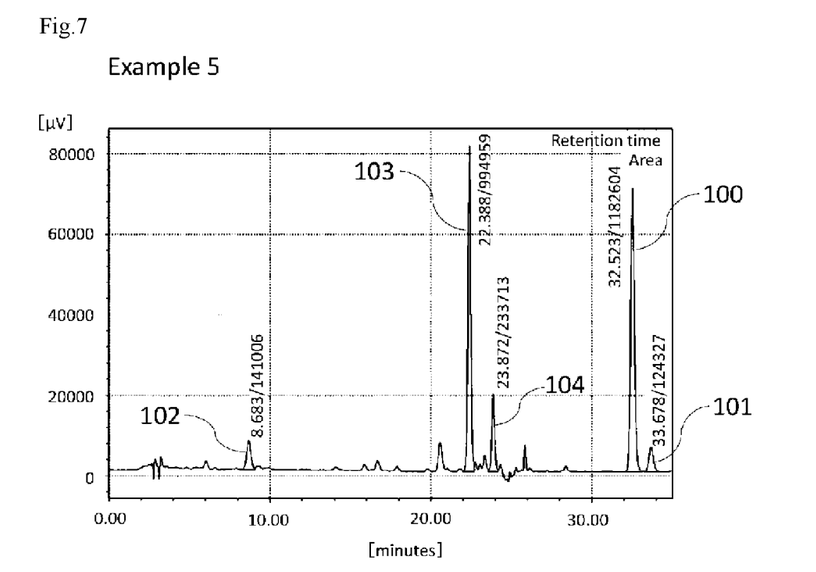
FIG. 7 is an HPLC chromatogram of a liquid obtained by dissolving the yellow-brown resinous melinjo extract obtained in Example 5 in 50% ethanol.
Figure 8:
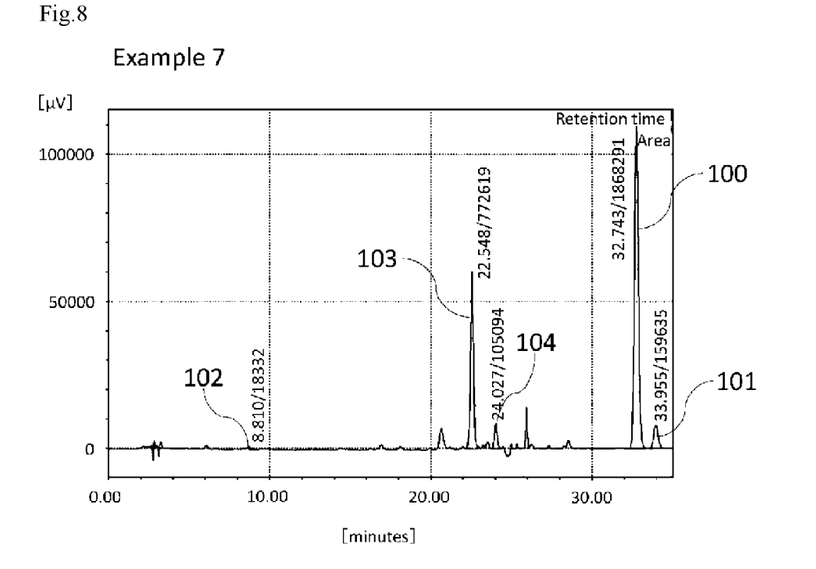
FIG. 8 is an HPLC chromatogram of a liquid obtained by dissolving the yellow-brown resinous melinjo extract obtained in Example 7 in 50% ethanol.
Figure 9:
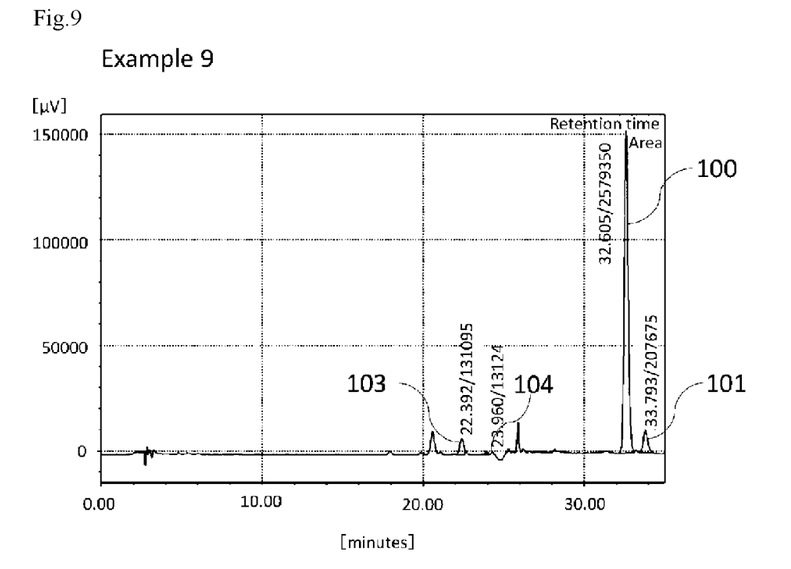
FIG. 9 is an HPLC chromatogram of a liquid obtained by dissolving the yellow-brown resinous melinjo extract obtained in Example 9 in 50% ethanol.
Figure 10:
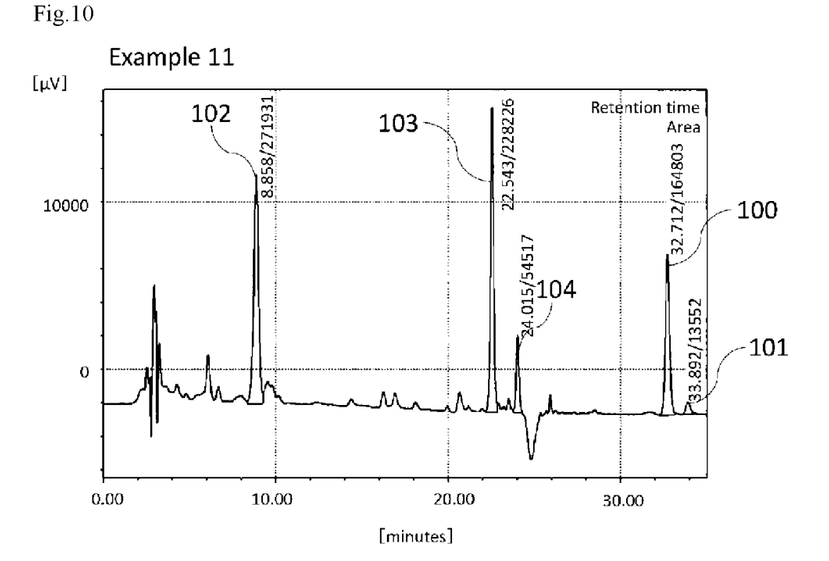
FIG. 10 is an HPLC chromatogram of a liquid obtained by dissolving the yellow-brown resinous melinjo extract obtained in Example 11 in 50% ethanol.
Figure 11:
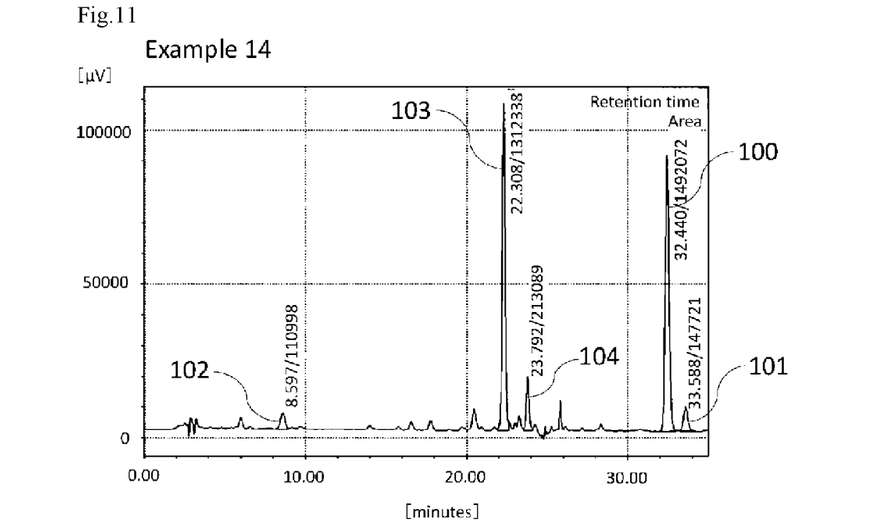
FIG. 11 is an HPLC chromatogram of a liquid obtained by dissolving the yellow-brown resinous melinjo extract obtained in Example 14 in 50% ethanol.
Figure 12:
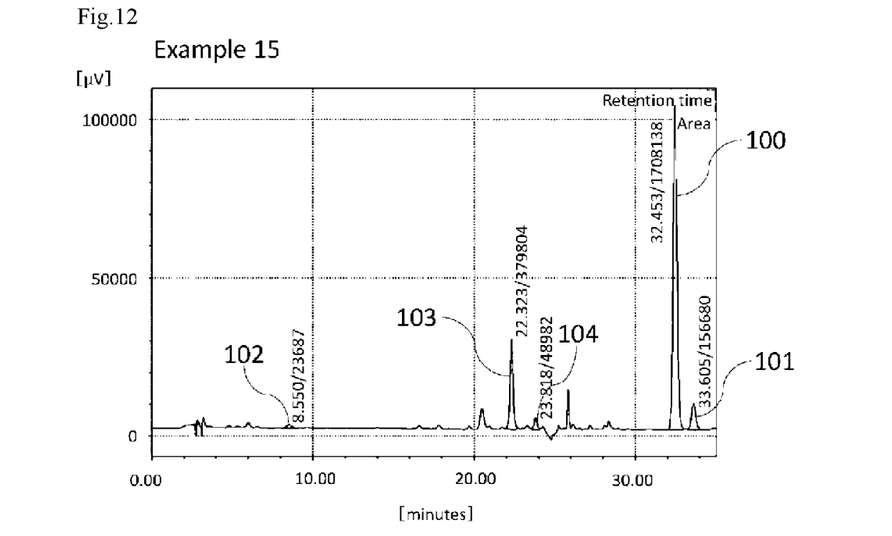
FIG. 12 is an HPLC chromatogram of a liquid obtained by dissolving the yellow-brown resinous melinjo extract obtained in Example 15 in 50% ethanol.
Figure 13:
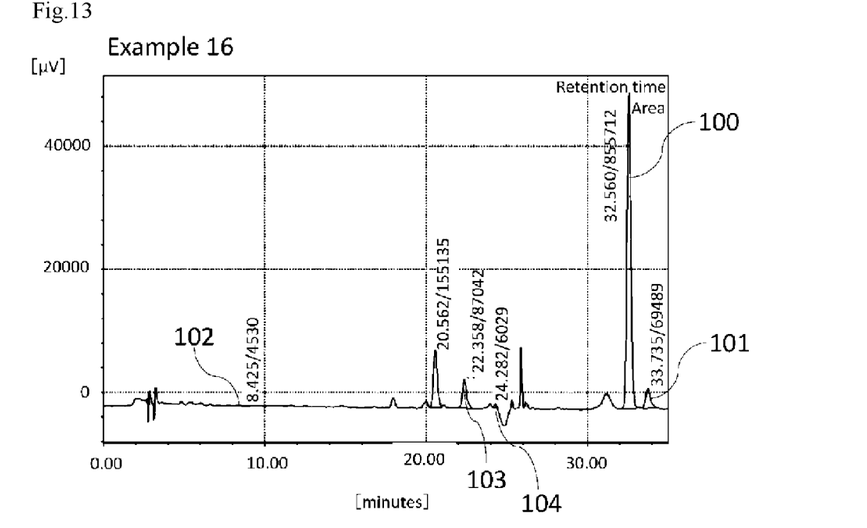
FIG. 13 is an HPLC chromatogram of a liquid obtained by dissolving the yellow-brown resinous melinjo extract obtained in Example 16 in 50% ethanol.
Figure 14:
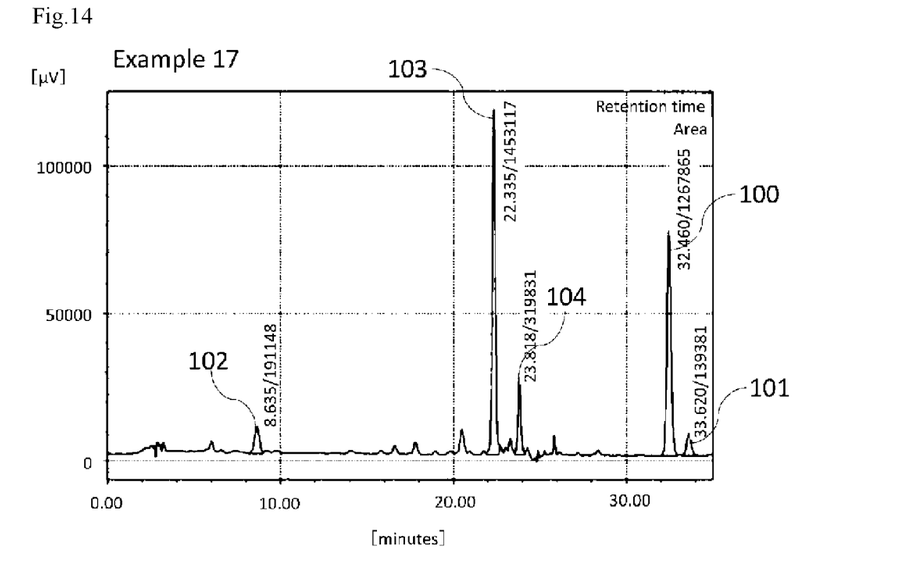
FIG. 14 is an HPLC chromatogram of a liquid obtained by dissolving the yellow-brown resinous melinjo extract obtained in Example 17 in 50% ethanol.

One part of melinjo powder crushed endosperms 1 kg of dried melinjo seeds by crusher was immerged in extraction solvent solved an acid and/or an emulsifier, and stirred at specified temperatures for specified days which are shown in Table 1. Solid content was separated by centrifugation to obtain immersion liquid. This liquid was concentrated under reduced pressure to prepare yellow-brownish resinous melinjo extracts (Comparative Example 1-3, Example 1-17). These melinjo extracts ware dissolved in 50 v/v % ethanol and carried out HPLC analysis to get those chromatograms. A 100GCA/TGA and GLA/GCA ware determined on the basis of GCA, GGA, TGA and GLA calculated on the chromatogram. The results of analysis are shown Table 2. The HPLC chromatograms of Comparative Example 1-3 and Example 1, 2, 4, 5, 7, 9, 11, 14, 15, 16 and 17 are shown FIG. 1-14. Room temperature means temperature without artificial control, and it was 13-25° C.

TABLE 2

| Extraction Condition | | GCA | GGA | TGA | 100 GCA/ TGA | GLA | GLA/ GCA |
|---|---|---|---|---|---|---|---|
| Comparative | 1 | 164803 | 554674 | 719477 | 22.9% | 13552 | 0.082 |
| Examples | 2 | 309191 | 698759 | 1007950 | 30.7% | 35534 | 0.115 |
| Examples | 3 | 190901 | 1513505 | 1704406 | 11.2% | 25931 | 0.136 |
| | 1 | 1710031 | 1822196 | 3532227 | 48.4% | 150395 | 0.088 |
| | 2 | 3450357 | 310623 | 3760980 | 91.7% | 299462 | 0.087 |
| | 3 | 1182356 | 2003080 | 3185436 | 37.1% | 117039 | 0.099 |
| | 4 | 1100074 | 952881 | 2052955 | 53.6% | 112768 | 0.103 |
| | 5 | 1182604 | 1369678 | 2552282 | 46.3% | 124327 | 0.105 |
| | 6 | 1264078 | 1654729 | 2918807 | 46.3% | 115037 | 0.091 |
| | 7 | 1868291 | 896045 | 2764336 | 67.6% | 159635 | 0.085 |
| | 8 | 3534769 | 146375 | 3681144 | 96.0% | 315872 | 0.089 |
| | 9 | 2579350 | 144219 | 2723569 | 94.7% | 207675 | 0.081 |
| | 10 | 1270585 | 376117 | 1646702 | 77.2% | 118900 | 0.094 |
| | 11 | 1273221 | 295068 | 1568289 | 81.2% | 110104 | 0.086 |

TABLE 1

| Extraction Condition | | | Extraction solvent | | Acid | Emulsifier |
|---|---|---|---|---|---|---|
| Comparative Examples | 1 | 50° C., 3 d | Water, 5 P | — | — | — |
| | 2 | 50° C., 3 d | Water, 2.5 P | Ethanol, 2.5 P | — | — |
| | 3 | 50° C., 3 d | | Ethanol, 5 P | — | — |
| Examples | 1 | 50° C., 2 d | Water, 2.5 P | Ethanol, 2.5 P | Acetic acid 0.01 P | — |
| | 2 | 50° C., 2 d | Water, 1 P | Ethyl acetate, 4 P | Acetic acid 0.01 P | — |
| | 3 | rt, 2 d | Water, 2.5 P | Acetonitrile, 2.5 P | Phosphoric acid 0.005 P | — |
| | 4 | rt, 2 d | Water, 5 P | — | — | Sucrose fatty acid ester(*1), 0.1 P |
| | 5 | rt, 2 d | Water, 5 P | — | — | Sucrose fatty acid ester(*2), 0.1 P |
| | 6 | rt, 2 d | Water, 5 P | — | — | Glycerin fatty acid ester(*3), 0.1 P |
| | 7 | 35° C., 2 d | Water, 5 P | — | Acetic acid 0.01 P | Glycerin fatty acid ester(*4), 0.1 P |
| | 8 | 50° C., 2 d | Water, 5 P | — | Acetic acid 0.01 P | Glycerin fatty acid ester(*4), 0.2 P |
| | 9 | 50° C., 2 d | Water, 5 P | — | Lactic acid, 0.01 P | Sorbitan(*5), 0.025 P |
| | 10 | rt, 2 d | Water, 2.5 P | Diethyl ethel, 2.5 P | Acetic acid 0.01 P | Glycerin fatty acid ester(*4), 0.1 P |
| | 11 | rt, 3 d | Water, 2.5 P | Ethyl acetate, 2.5 P | Acetic acid 0.01 P | Glycerin fatty acid ester(*4), 0.1 P |
| | 12 | 50° C., 3 d | Water, 2 P | Tetrahydrofuran, 3 P | Acetic acid 0.01 P | Glycerin fatty acid ester(*3), 0.1 P |
| | 13 | 35° C., 3 d | Water, 1 P | Acetone, 4 P | Acetic acid 0.01 P | Glycerin fatty acid ester(*6), 0.1 P |
| | 14 | rt, 3 d | Water, 3.5 P | Pyridine, 1.5 P | Hydrochloric acid 0.5 P | Glycerin fatty acid ester(*2), 0.1 P |
| | 15 | 50° C., 3 d | Water, 3.5 P | N,N-Dimetylacetamide 1.5 P | Acetic acid 0.01 P | Glycerin fatty acid ester(*2), 0.1 P |
| | 16 | 50° C., 2 d | Water, 5 P | — | Acetic acid 0.005 P | Branched cyclodextrin (*7), 0.1 P |
| | 17 | 40° C., 3 d | | Ethanol, 4 P | Acetic acid 0.01 P | Sucrose fatty acid ester(*8), 0.2 P | d: day P: part rt: room temperature
*1 Sucrose laurate (HLB 16, Ryoto Sugar Ester L-1695, Mitsubishi-Chemical Foods Corporation)
*2 Mixture of Decaglycerol monolaurate (HLB 15.5, POEM J-0021, Riken Vitamin Co., Ltd.) and glycerol monooleate (HLB 4.3, EMARGI OL-100H, Riken Vitamin Co., Ltd.)
*3 Decaglycerol monostearate (HLB 12, POEM J-0081HV, Riken Vitamin Co., Ltd.)
*4 Decaglycerol monolaurate
*5 Polyoxyethylene sorbitan monooleate (HLB15, EMASOL O-120V, Kao Chemicals)
*6 Glycerol monooleate
*7 Isoerito P (ENSUIKO Sugar Refining Co. Ltd.)
*8 Sucrose stearate (HLB 15, Ryoto Sugar Ester L-1570, Mitsubishi-Chemical Foods Corporateion)

TABLE 2-continued

| Extraction Condition | GCA | GGA | TGA | 100 GCA/ TGA | GLA | GLA/ GCA |
|---|---|---|---|---|---|---|
| 12 | 1003501 | 153210 | 1156711 | 86.8% | 96098 | 0.096 |
| 13 | 2295142 | 1001508 | 3296650 | 69.6% | 216987 | 0.095 |
| 14 | 1492072 | 1636425 | 3128497 | 47.7% | 147721 | 0.099 |
| 15 | 1708138 | 452473 | 2160611 | 79.1% | 156680 | 0.092 |
| 16 | 855712 | 242177 | 1097889 | 77.9% | 69489 | 0.081 |
| 17 | 1267865 | 1964096 | 3231961 | 39.2% | 139381 | 0.110 |

The GLA/GCA ratios of melinjo extracts of comparative examples 1-3 extracted by conventional extraction method disclosed in patent document 1 ware 0.082-0.136, and those 100GCA/TGA ratios ware less than 31%.

On the other hand, the GCA/TGA ratios of melinjo extracts of examples 1-16 ware not less than 37%, and those GLA/GCA ratios ware not more than 0.105.

It is noted from the comparative Examples 1-3 (FIGS. 1-3) that the peak area ratios of gnetin C to gnemonoside A is of the order of 0.16-1.4 in the conventional extraction method of the melinjo extracts (Comparative Example 1: peak area ratio is 0.61, Example 2: peak area ratio is 1.4, Example 3: peak area ratio is 0.16).

On the other hand, chromatograms of melinjo extracts produced by production method of the present invention in Examples 1, 2, 4, 5, 7, 9, 11, 14-16 (FIG. 4-13) shows that the peak area ratios of gnetin C to gnemonoside A is at least 6.6. Gnemonoside A could not be detected on chromatograms of Example 2 and 9.

That is to say, gnetin C increases and gnemonoside A decreases in melinjo extracts according to the production method of the present invention. It was found from the above result that the production method of the present invention could be produced a melinjo extract which contained more gnetin C than the conventional extraction method.

Results of examples 1-3 shows that the presence of acids in extraction solvent accelerates solvolysis reaction by glucosidase containing in endosperm and can be allowed to produce the gnetin C high content melinjo extract. The results of examples 1-3 also indicates that solvolysis reaction of gnemonosides C and D by the glucosidase is rate limiting, but solvolysis reaction of gnemonosides C and D is accelerated on the basis of hydrogen ion increased by addition of acids, so that a gnetin C high content melinjo extract can be produced.

Further, the glucosidase operating in system of water and alcohol results in solvolysis reaction of readily water-soluble gnemonoside A and gnemonoside C and D which are soluble in water and alcohol and liberates sparingly water-soluble gnetin C. In the presence of aprotic organic solvent, it is inferred that the organic solvent surrounds the periphery of gnetin C and removes gnetin C from active site of glucosidase, so that the solvolysis reaction is accelerated, and a gnetin C high content melinjo extract can be produced.

In the case of coexistence with emulsifiers in the extraction solvent, it is inferred from result of Example 4-6 that the emulsifiers form micelles in the reaction system, and the solvolysis reaction is accelerated owing to the micelles removing gnetin C from the active site of glucosidase by incorporating gnetin C therein, so that a gnetin C high content melinjo extract can be produced.

In the case of coexistence with cycrodextrin in the extraction solvent, it is inferred from clathration of gnetin C that the solvolysis reaction is likewise accelerated.

The results of Example 7-17 show that combination of acids, organic solvents, emulsifiers and cyclic oligosaccharides in the extraction solvent leads to rise of the content of gnetin C by their combined action.

Specially, Muslim who is banned intake of alcohol by halal can take and coat melinjo extracts in these examples, since sparingly water-soluble gnetin C is efficiently generated in spite of non-inclusion of alcohol as a extraction solvent in Example 8 and 9.

Example 18 (Production of Extract)

Melinjo powder 50 g prepared in Test 1 was added to water 250 mL containing citric acid 0.2 g, stirred at 60° C. for 2 days and then filtered. This filtrate was analyzed in a similar manner as Test 1 to give GCA of 2609114, GGA of 3138350, TGA of 5747464, 100GCA/TGA of 45.4%, GLA of 187489 and GLA/GCA of 0.072.

The filtrate was concentrated to get concentrate to which ethanol 50 mL was added and filtered. This filtrate was concentrated under reduced pressure to yield 0.9 g of a gnetin C high content melinjo extract as pale yellowish brown resinous substance. The gnetin C content was 25.2%.

Example 19 (Production of Extract)

Melinjo powder 30 g prepared in Test 1 was added to water 150 mL containing adipic acid 0.1 g, Sucrose stearate (HLB 15, Ryoto Sugar Ester S-1570, Mitsubishi-Chemical Foods Corporation) 1 g and propylene glycol monopalmitate (HLB 3.8, RIKEMAL PP-100, Riken Vitamin Co., Ltd.) 0.2 g, stirred at 50° C. for 2 days and then filtered. This filtrate was analyzed in a similar manner as Test 1 to give GCA of 2295142, GGA of 1001508, TGA of 3296650, 100GCA/TGA of 69.6%, GLA of 216987 and GLA/GCA of 0.095.

The filtrate was concentrated under reduced pressure to get concentrate to which acetone 30 mL was added and filtered. This filtrate was concentrated under reduced pressure to yield 0.7 g of a gnetin C high content melinjo extract as pale yellowish brown resinous substance. The gnetin C content was 72.8%.

Example 20 (Production of Extract)

Melinjo powder 70 g prepared in Test 1 was added to mixture of 0.1 w/v % sulfuric acid 300 mL, propylene glycol 40 mL, methylene chloride 30 mL and 2-aminoethanol 0.3 mL, stirred at 60° C. for 2 days and then filtered with filter cloth. This filtrate was analyzed in a similar manner as Test 1 to give GCA of 311326, GGA of 443912, TGA of 755238, 100GCA/TGA of 41.2%, GLA of 31935 and GLA/GCA of 0.103. The filtrate was extracted twice with ethyl acetate 200 mL. The ethyl acetate layer was washed with a saturated saline solution, dried with magnesium sulfate and then concentrated under reduced pressure to yield 0.6 g of a gnetin C high content melinjo extract as pale yellowish brown resinous substance. The gnetin C content was 47.8%.

Example 21 (Production of Extract)

Melinjo powder 50 g prepared in Test 1 was added to mixture of methanesulfonic acid 0.1 g, water 120 mL and cellosolve acetate 130 mL, stirred at 50° C. for 3 days and then filtered with filter cloth. After addition of water 250 mL, the filtrate was allowed to absorb in polystyrene resin (DIAION, SEPABEADS, Mitsubishi Chemical Corporation). This resin was washed and permitted to desorb with methanol. This elute was concentrated under reduced pressure to yield 0.3 g of a gnetin C high content melinjo extract as pale yellowish brown resinous substance. The extract was analyzed in a similar manner as Test 1 to give GCA of 1497851, GGA of 0, TGA of 1497851, 100GCA/TGA of 100%, GLA of 143699, GLA/GCA of 0.096. Gnetin C content in the extract was 93.5%.

Example 22 (Production of Extract)

Melinjo powder 30 g prepared in Test 1 was added to mixture of trifluoroacetic acid 0.1 mL, Sucrose laurate (Ryoto Sugar Ester L-1695, Mitsubishi-Chemical Foods Corporation) 0.9 g, sorbitan caprylate (HLB10.5, POEM C-250, Riken Vitamin Co., Ltd.) 0.3 g, water 120 mL, glycerol 30 mL and cyclohexane 30 mL stirred at 50° C. for 3 days and then filtered with filter cloth. The filtrate was extracted with ethyl acetate 100 mL.

The organic layer was concentrated under reduced pressure to yield 0.4 g of a gnetin C high content melinjo extract as pale yellowish brown resinous substance. The extract was analyzed in a similar manner as Test 1 to give GCA of 2449550, GGA of 226117, TGA of 2675667, 100GCA/TGA of 91.5%, GLA of 268768 and GLA/GCA of 0.110. Gnetin C content of the extract was 68.6%.

The obtained extract was purified by silica gel column chromatography (eluting solvent: methylene chloride-methanol system) to get gnetin C 0.2 g of purity 98.8%.

Example 23 (Production of Extract)

Melinjo powder 30 g prepared in Test 1 was added to mixture of sodium laurate (Runak L-98, Kao Corporation) 0.5 g, polyoxyethylen sorbitan monooleate (HLB 15.0, Emazol O-120V, Kao Corporation) 0.5 g, water 90 mL, dimethyl sulfoxide 10 mL and ethyl acetate 200 mL, stirred at room temperature for 2 days and then filtered with filter cloth. To the obtained filtrate 1 w/v % hydrochloric acid 1 mL and ethyl acetate 200 mL ware added and extracted. This organic layer was concentrated under reduced pressure to yield 0.4 g of gnetin C high content a melinjo extract as pale yellowish brown resinous substance. The extract was analyzed in a similar manner as Test 1 to give GCA of 1221938, GGA of 1463346, TGA of 2685284, 100GCA/TGA of 45.5%, GLA of 97441 and GLA/GCA of 0.080. Gnetin C content in the extract was 30.7%.

Example 24 (Production of Extract)

Dried melinjo fruits 100 g ware crushed and added to mixture of decaglycerol monolaurate (HLB 15.5, POEM J-0021, Riken Vitamin Co., Ltd.) 1 g, soybean lecithin (Beisis LP-20B, Nisshin OilliO Group, Ltd.) 0.3 g, methyl cellosolve 20 mL, methylethylketone 30 mL and water 500 mL, stirred at 40° C. for 2 days and then centrifuged. The supernatant was separated. Water 300 mL was added to the precipitate, thoroughly stirred and centrifuged. This and the former supernatant ware combined and extracted with ethyl acetate 300 mL. This organic layer was concentrated under reduced pressure to yield 1.2 g of a gnetin C high content melinjo extract as pale reddish orange resinous substance. The extract was analyzed in a similar manner as Test 1 to give GCA of 2188861, GGA of 202423, TGA of 2391284, 100GCA/TGA of 91.5%, GLA of 196693 and GLA/GCA of 0.090. Gnetin C content in the extract was 41.7%.

Example 25 (Production of Extract)

Dried melinjo fruits 50 g ware crushed and added to mixture of decaglycerol monostearate (HLB 12, POEM J-0081HV, Riken Vitamin Co., Ltd.) 0.5 g, dioxane 30 mL, boron trifurolide diethyl ether complex 0.05 mL and water 200 mL, stirred at 60° C. for 30 hours and then centrifuged. The supernatant was separated. Water 150 mL was added to the precipitate, thoroughly stirred and centrifuged. This and the former supernatant ware combined, added to water 500 mL and then allowed to absorb in polystyrene resin (DIAION, SEPABEADS, Mitsubishi Chemical Corporation). This resin was washed and permitted to desorb with ethanol. This elute was concentrated under reduced pressure to yield 0.6 g of a gnetin C high content melinjo extract as pale reddish orange resinous substance. The extract was analyzed in a similar manner as Test 1 to give GCA of 1555812, GGA of 123689, 100TGA of 1679501, GCA/TGA of 92.6%, GLA of 137847 and GLA/GCA of 0.089. Gnetin C content in the extract was 61.3%.

Example 26 (Production of Extract)

Undried melinjo fruits 100 g ware shredded and added to solvent of water 170 mL containing lactic acid 0.25 mL, sucrose stearate (HLB 16, Ryoto Sugar Ester S-16, Mitsubishi-Chemical Foods Corporation) 1.0 g and tetraglycerol monostearate (HLB 5.6, POEM J-4081V, Riken Vitamin Co., Ltd.) 0.1 g, stirred at 50° C. for 24 hours and then centrifuged. The supernatant was separated. Water 150 mL was added to the precipitate, thoroughly stirred and centrifuged. This and the former supernatant ware combined, added to the same amount of water and then allowed to absorb in polystyrene resin (DIAION, SEPABEADS, Mitsubishi Chemical Corporation). This resin was washed and permitted to desorb with ethanol. This elute was concentrated under reduced pressure to yield 0.3 g of a gnetin C high content melinjo extract as pale reddish orange resinous substance. The extract was analyzed in a similar manner as Test 1 to give GCA of 2582781, GGA of 126005, TGA of 2708786, 100GCA/TGA of 95.3%, GLA of 265565 and GLA/GCA of 0.103. Gnetin C content in the extract was 79.4%.

Example 27 (Production of Extract)

Undried raw melinjo seeds 70 g was shredded and added to ethanol 170 mL containing acetic acid 0.4 mL, stirred at 50° C. for 3 days and then filtered with filter cloth. This filtrate was concentrated under reduced pressure to yield 0.5 g of a gnetin C high content melinjo extract as pale brown resinous substance. The extract was analyzed in a similar manner as Test 1 to give GCA of 1221938, GGA of 2074243, TGA of 3296181, 100GCA/TGA of 37.1% which was 3 times higher than that of Example 1 in condition 1C, GLA of 97441 and GLA/GCA of 0.080. Gnetin C content in the extract was 26.1%.

Example 28 (Production of Extract)

Emping 50 g, which was prepared by crush and dryness of endosperms obtained by heating seeds and peeling their seed-coat, and residual endosperms in filter cloth gotten by filtration in Example 21 described above ware added to water 400 mL containing decaglycerol monolaurate (HLB 15.5, POEM J-0021, Riken Vitamin Co., Ltd.) 1.5 g and acetic acid 0.2 mL, stirred at 40° C. for 3 days and then filtered with filter cloth. This filtrate was concentrated under reduced pressure to obtain concentrate. Ethanol 50 mL was added to this concentrate and filtered. This filtrate was concentrated under reduced pressure to yield a melinjo extract 2.3 g as pale yellowish brown resinous substance. The extract was analyzed in a similar manner as Test 1 to give GCA of 2346693, GGA of 163610, TGA of 2510303, 100GCA/TGA of 93.5%, GLA of 226002 and GLA/GCA of 0.096. Gnetin C content in the extract was 32.5%.

Example 29 (Production of Extract)

Crushed endosperm 2 kg of dried melinjo seeds was added to water 8 L containing acetic acid 0.8 g and decaglycerol monolaurate 20 g, stirred at 50° C. for 2 days and then filtered with filter cloth. This filtrate was concentrated under reduced pressure to obtain syrup-like substance. Acetone 2 L was added to this substance and filtered out insoluble material. This filtrate was concentrated under reduced pressure to yield 44.8 g of a gnetin C high content melinjo extract as pale yellowish brown resinous substance. The extract was analyzed in a similar manner as Test 1 to give GCA of 500069, GGA of 0, TGA of 500069, GCA/TGA of 100%, GLA of 196693 and GLA/GCA of 0.047. Gnetin C content in the extract was 42.6%.

Example 30 (Production of Powdery Composition Containing Melinjo Extract)

Crushed endosperm 50 g of dried melinjo seeds was added to water 250 mL containing adipic acid 0.03 g and high branched cyclodextrin (CRUSTER DEXTRIN, Glico Nutrition Co., Ltd.) 6 g, stirred at 50° C. for 2 days and then separated with high speed centrifuge. This supernatant was lyophilized to yield powder 11.1 g of a gnetin C high content melinjo extract. This powder was analyzed in a similar manner as Test 1 to give GCA of 14731790, GGA of 810026, TGA of 15541816, 100GCA/TGA of 94.8%, GLA of 1247201 and GLA/GCA of 0.085. Gnetin C content in the extract was 5.3%.

Example 31 (Production of Powdery Composition Containing Melinjo Extract)

The melinjo extract 10 g prepared in the said Example 29 was dissolved in water 80 mL. Dextrin 10 g was added to this solution, mixed and lyophilized to yield powder 19.4 g. Granules can be produced by mixing this powder with vehicle and binder. Hard capsules can be produced by mixing this powder with vehicle and lubricant. Tablets can be produced by mixing this powder with vehicle, disintegrator and lubricant.

It is possible to mix this powder with powder soft drinks containing a blended arbitrary base material usually used, liquid products such as liquid soft drink, juice, coffee, black tea, liqueur, milk, whey beverage, lactobacillus beverage, yoghurt and the like; solid products such as candy, caramel, chewing gum, chocolate, gummi, ice cream, pudding, egg products, yokan (soft adzuki-bean jelly), mizu-yokan (soft adzuki-bean jelly), okaki (small rice cracker), rice cake, rice dumpling, rice cracker, crape, okonomiyaki (pancake), bread, cookie, noodles, hamburger, water paste, tempura, fermented foods, furikake (rice seasoning) and the like. Further, it is possible to mix the powder with pet foods and feedstuffs.

Example 32 (Production of Pasty Composition Containing Melinjo Extract)

The gnetin C high content melinjo extract 10 g prepared in the said Example 29 was heated and mixed with soybean lecithin 3 g and olive oil 7 g to yield extract past 20 g. Soft capsules can be produced by packing this past. Soft capsules can be produced by packing mixture of this past and fat and oil containing EPA (eicosapentaenoic acid) and DHA (docosahexaenoic acid). Further, it is possible to mix the past with pet foods and feedstuffs.

INDUSTRIAL APPLICABILITY

The present invention can produce a melinjo extract having the enhanced content of gnetin C manifesting various actions such as an antioxidant action, an antibacterial action, a lipase inhibitory action, an amylase inhibitory action, an angiogenesis suppressive action, an antitumor action, an action of inducing apoptosis of human leukemia cells, an immunostimulating action, an immunomodulating action, an anti-obesity/diabetes improving action, a tyrosinase inhibitory action, a melanin biosynthesis inhibitory action, a vascular aging suppressive action, a sirtuin activating action, a high density lipoprotein (HDL) cholesterol increasing action, a uric acid level lowering action, a periodontal disease exacerbation preventing action, an atrophic skin suppressive action and the like. The gnetin C high content melinjo extract of the present invention is useful for prevention and treatment of aging, cancer, leukemia, malignant melanoma, periodontal disease, pollen disease, metabolic syndrome, diabetes mellitus, cardiac disease, brain disease, allergic disease, autoimmune disease, atopic dermatitis, hyperuricemia, gout and the like. Further, since melinjo is often eaten in Southeast Asia, the composition can be ingested or administered with confidence, in the usual food form in daily life, as a prevention and treatment agent for various diseases as described above.

By using the gnetin C high content melinjo extract-containing composition having the enhanced content of gnetin C of the present invention as the feeding stuff for animals such as pets and domestic animals, also pets recently showing a tendency of an increase in metabolic syndrome can be treated without so much increasing the burden of the feeder.

EXPLANATION OF NUMERALS

100 peak of gnetin C
101 peak of gnetin L
102 peak of gnemonoside A
103 peak of gnemonoside D
104 peak of gnemonoside C

The invention claimed is:
1. A production method of a melinjo extract, comprising an extraction step of extracting an extract from melinjo fruit by using an extraction solvent which is a mixed solvent obtained by blending at least one of an emulsifier, a cycrodextrin and an acid into water and/or an organic solvent, and a temperature of the extraction solvent in extracting is 10 to 70° C.
2. The production method according to claim 1, wherein the melinjo fruit is melinjo endosperm.
3. The production method according to claim 1, wherein the organic solvent is one or more selected from ethanol, ethyl acetate and acetone.
4. The production method according to claim 1, wherein the emulsifier is one or more selected from glycerin fatty acid ester, sucrose fatty acid ester, sorbitan fatty acid ester, soybean lecithin and sodium stearate.

5. The production method according to claim 1, wherein the acid is one or more selected from acetic acid, lactic acid, citric acid, adipic acid, hydrochloric acid and phosphoric acid.

6. The production method according to claim 2, wherein the organic solvent is one or more selected from ethanol, ethyl acetate and acetone.

7. The production method according to claim 2, wherein the emulsifier is one or more selected from glycerin fatty acid ester, sucrose fatty acid ester, sorbitan fatty acid ester, soybean lecithin and sodium stearate.

8. The production method according to claim 2, wherein the acid is one or more selected from acetic acid, lactic acid, citric acid, adipic acid, hydrochloric acid and phosphoric acid.

9. The production method according to claim 1, wherein the cycrodextrin is cyclodextrin.

10. A production method of a melinjo extract, comprising an extraction step of extracting an extract from melinjo fruit by using an extraction solvent which is a mixed solvent obtained by blending at least one of an emulsifier, a cycrodextrin and an acid into water and/or an organic solvent, wherein the acid is one or more selected from acetic acid, lactic acid, citric acid, adipic acid, hydrochloric acid, and phosphoric acid.

* * * * *